United States Patent [19]

Osada et al.

[11] Patent Number: 4,721,670
[45] Date of Patent: Jan. 26, 1988

[54] ANALYTICAL REAGENT, ANALYTICAL METHOD, AND MULTILAYER CHEMICAL-ANALYTICAL ELEMENT

[75] Inventors: Chiaki Osada; Harumi Katsuyama, both of Saitama, Japan

[73] Assignee: Fuji Photo Film Co., Ltd., Kanagawa, Japan

[21] Appl. No.: 745,914

[22] Filed: Jun. 18, 1985

[30] Foreign Application Priority Data

Jun. 19, 1984 [JP] Japan ................................. 59-124412

[51] Int. Cl.⁴ ..................... C12Q 1/28; C07D 403/00; G01N 33/00
[52] U.S. Cl. ........................................ 435/28; 435/805; 435/810; 422/56; 422/57; 548/336; 436/135
[58] Field of Search .................. 435/28, 177, 180, 182, 435/805, 810; 422/56, 57; 548/336; 436/135

[56] References Cited

U.S. PATENT DOCUMENTS

| | | | |
|---|---|---|---|
| 3,992,158 | 11/1976 | Przybylowicz | 435/28 |
| 4,089,747 | 5/1978 | Bruschi | 435/28 |
| 4,452,887 | 6/1984 | Kitajima et al. | 435/805 |

FOREIGN PATENT DOCUMENTS 0045557  3/1983  Japan ................................. 435/28

*Primary Examiner*—Esther M. Kepplinger
*Attorney, Agent, or Firm*—Jules E. Goldberg

[57] ABSTRACT

A novel imidazole derivative type reagent for analysis of hydrogen peroxide, a method of analysis of hydrogen peroxide using the same, a method of analysis of peroxidase using the same, and a multilayer chemicalanalytical element containing the same are disclosed.

The imidazole derivative has the formula (I):

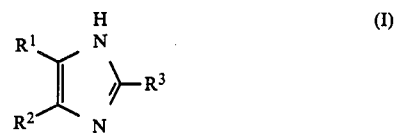

wherein $R^1$ and $R^2$ represent an aryl group or a substituted aryl group, and $R^1$ and $R^2$ are identical with or different from each other, and $R^3$ represents 2- or 3-pyrrolyl group, a substituted 2- or 3-pyrrolyl group, 2- or 3-indolyl group, or a substituted 2- or 3-indolyl group.

17 Claims, No Drawings

ANALYTICAL REAGENT, ANALYTICAL METHOD, AND MULTILAYER CHEMICAL-ANALYTICAL ELEMENT

BACKGROUND OF THE INVENTION

1. Field of the Invention

The present invention relates to a novel reagent for analysis of hydrogen peroxide, a method of analysis of hydrogen peroxide using the same, a method of analysis of peroxidase using the same, and a multilayer chemicalanalytical element containing the same. More particularly, the present invention relates to a novel color forming compound which is capable of forming a color in the presence of hydrogen peroxide and a catalytic substance having an oxidizing activity, such as peroxidase, a method for colorimetric quantitative analysis of hydrogen peroxide using the same, and a multilayer chemical-analytical element which contains the same and is suitably employable in quantitative analysis of hydrogen peroxide or an analyte (substance to be analyzed) capable of forming hydrogen peroxide, as well as in quantitative analysis of peroxidase activity.

2. Description of Prior Arts

Enzymic analytical methods in clinical test have been highly valued in their specific reactivity and have rapidly come into wide use in recent years. Particularly, in quantitative analyses of glucose, uric acid, cholesterol, triglyceride, lactic acid, creatinine, free fatty acid, glutamate-pyruvate transaminase, glutamate-oxaloacetate transaminase, cholinesterase, creatine phosphokinase and lactate dehydrogenase in body fluid and urine, there are frequently used methods of quantitatively analyzing such object (analyte) by causing said analyte or a final intermediate product derived from the analyte to react with an oxidase therefor and determining thus produced hydrogen peroxide.

As the methods of quantitative determination of hydrogen peroxide, there are known, for example, methods disclosed in the specifications of Japanese Patent Provisional Publication Nos. 50(1975)-115892, 53(1978)-110897, 54(1979)-25892, 55(1980)-20471, 55(1980)-92696, 55(1980)-121149, 55(1980)-131400, 56(1981)-37557, 56(1981)-39072, 56(1981)-42599, 57(1982)-142562, 57(1982)-150399, etc. These specifications disclose colorimetric methods comprising converting a chromogen such as o-tolidine, 2,7-diaminofluorene, N,N-dimethyl-p-phenylenediamine, o-dianisidine or o-aminophenol into a colored substance through oxidation, as well as colorimetric methods comprising converting a chromogen such as a combination of 4-aminoantipyrine with phenol, N,N-dialkylaniline or N,N-dialkyltoluidine, a combination of 3-methyl-2-benzthiazolinone hydrazone with o-tolidine, N,N-dimethylanline or N,N-diethylaniline, or 4-methoxy-1-naphthol capable of forming a dimer or its derivative into a colored substance by oxidative condensation.

The methods using these compounds are disadvantageous in determination of minor constituents (analyte), since these compounds require two molar hydrogen peroxide to form one molar colored substance (dye). For this reason, a reagent for quantitatively analyzing hydrogen peroxide, which requires only one molar hydrogen peroxide to form one molar dye is desired.

The inventor has already investigated such a reagent for analysis of hydrogen peroxide, which comprises an imidazole derivative having the formula (I):

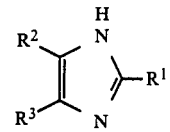

wherein $R^1$ is an aryl group substituted with hydroxyl group at the ortho- or para-position, $R^2$ is an unsubstituted or substituted aryl group, and $R^3$ is an unsubstituted or substituted alkyl or an unsubstituted alkenyl group, the method of analysis of hydrogen peroxide using the same, the method of analysis of peroxidase using the same, and a multilayer chemical-analytical element containing the same (U.S. patent application Ser. No. 6/601,632).

SUMMARY OF THE INVENTION

An object of the present invention is to provide a highly sensitive reagent advantageously employable for quantitative determination of hydrogen peroxide, which can form one molar dye with one molar hydrogen peroxide under the catalytic action or coupling reaction of peroxidase.

Another object of the present invention is to provide a method of quantitative determination of hydrogen peroxide using the above-mentioned reagent.

A further object of the present invention is to provide a multilayer chemical-analytical element for quantitative determination of hydrogen peroxide, which has a reagent layer containing the above-identified reagent.

The present inventors have discovered that the above objects can be achieved using a compound having the formula (I):

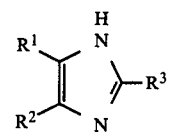

wherein $R^1$ and $R^2$ represent an aryl group or a substituted aryl group, and $R^1$ and $R^2$ are identical with or different from each other, and $R^3$ represents 2- or 3-pyrrolyl group, a substituted 2- or 3-pyrrolyl group, 2- or 3-indolyl group, or a substituted 2- or 3-indolyl group.

DETAILED DESCRIPTION OF THE INVENTION

The substituted aryl groups represented by $R^1$ and $R^2$ in the formula (I) may have one or more substituents selected from the group consisting of halogen atom (chlorine atom, bromine atom, etc.), a hydroxyl group, cyano group, an alkoxy group, a monoalkylamino group and a dialkylamino group, and when either or both of the substituted aryl groups have two or more substituents, they may be identical with or different from each other.

Preferred examples of the substituents represented by $R^1$ and $R^2$ are phenyl group, 4-methoxyphenyl group, 4-ethoxyphenyl group, 4-(dimethylamino) phenyl group and 4-(diethylamino) phenyl group.

The substituted 2- or 3-pyrrolyl group and the substituted 2- or 3-indolyl group represented by $R^3$ may have one or more substituents selected from the group consisting of a halogen atom (chlorine atom, bromine atom, etc.), cyano group, an alkyl group, a substituted alkyl group, an aryl group, hydroxyl group, carboxyl group, nitro group, an alkylsulfonylamino group, an arylsulfonylamino group, an alkoxy group, an alkoxycarbonyl group, an aryloxy group, a monoalkylamino group, a dialkylamino group, carbamoyl group, a N-alkylcarbamoyl group, an alkylsulfonyl group and sulfamoyl grpup. When the substituted group represented by $R^3$ has two or more substituents, they may be identical with or different from each other. Among these substituents, the aryl group, the halogen atom, the alkoxy group, cyano group and nitro group are preferable with respect to the synthesis of the compound (I) and its characteristics. Preferably aryl group is phenyl group and hydroxyphenyl group. Preferable alkyl group is methyl group and ethyl group, and preferable alkoxy group is methoxy group and ethoxy group.

Preferred examples of the substituent represented by $R^3$ are 2-pyrrolyl group, 3-indolyl group, 2-chloro-3-indolyl group, 5-chloro-3-indolyl group, 5-cyano-3-indolyl group, 5-nitro-3-indolyl group, 2-phenyl-3-indolyl group, 2-methoxycarbonyl-3-indolyl group, 2-ethoxycarbonyl-3-indolyl group, 5-methoxycarbonyl-3-indolyl group and 5-ethoxycarbonyl-3-indolyl group.

Preferred compounds of the formula (I) are illustrated below. However, it is not intended that the compounds of the present invention be limited to the illustrated compounds. in the following formulas, Me represents methyl group, Et represents ethyl group and Ph repressents phenyl group.

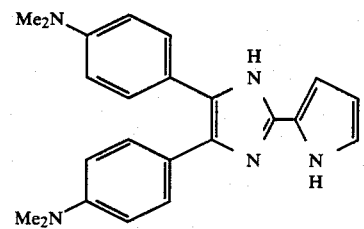
(1)

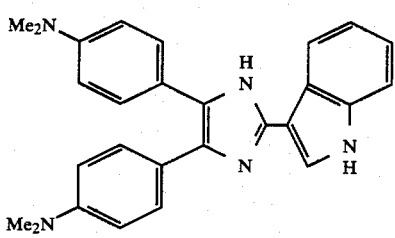
(2)

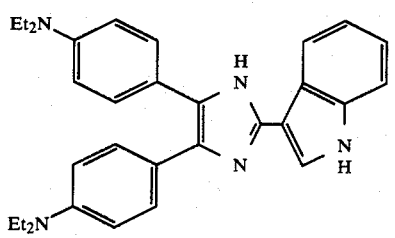
(3)

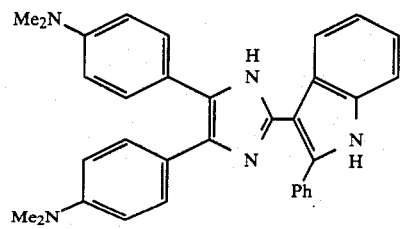
(4)

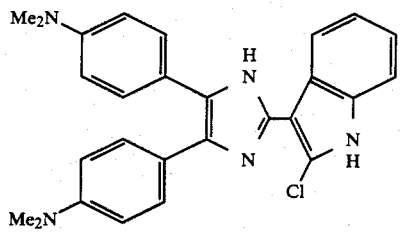
(5)

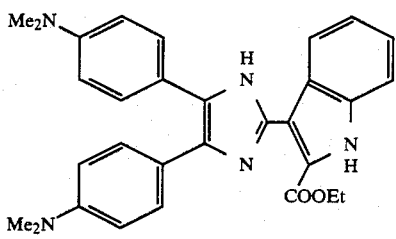
(6)

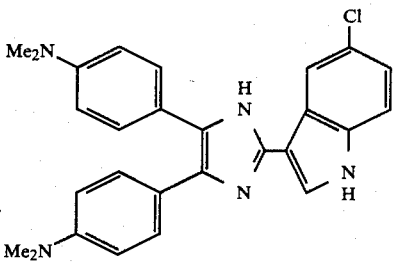
(7)

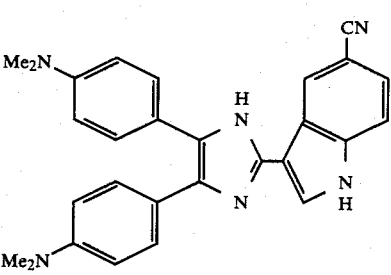
(8)

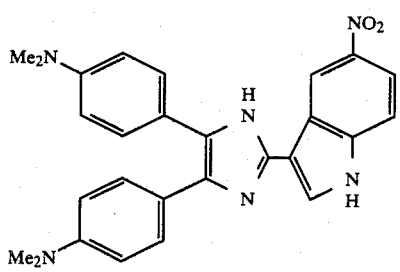
(9)

-continued

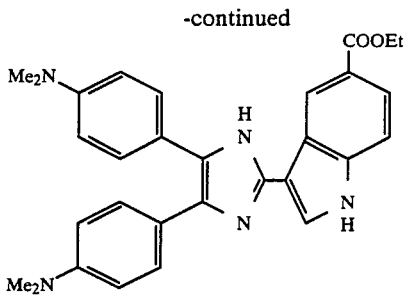

The novel compounds having the formula (I) can by synthesized according to the method described in U.S. Pat. No. 3,297,710. The following synthesis examples illustrate the preparation of the compounds having the formula (I). The compounds which are not exemplified can be synthesized in similar manners to those of the synthesis examples.

Synthesis Example 1

Synthesis of 2-(2-phenyl-3-indolyl)-4,5-di[4-dimethylamino)phenyl-]imidazole (compound (4))

2.2 g of bis[p-(dimethylamino)phenyl]ethanedione, 2.8 g of 2-phenyl-3-formylindole and 5 g of ammonium acetate were refluxed in 17 ml of glacial acetic acid for two hours by heating to effect the reaction. After cooling, the reaction mixture was added dropwise to the mixture of 20 ml of aqueous ammonia and 150 ml of water to precipitate yellowish green crystals. The crystals were collected by filtration, and washed with water. After drying, they were recrystallized with benzene-ethyl acetate ester (1:1) to obtain 3.9 g of the compound (4). Melting point; 228°–231° C.

SYNTHESIS EXAMPLE 2

Synthesis of 2-(5-chloro-3-indolyl)-4,5-di[4-(dimethylamino)phenyl-]imidazole (Compound (7))

2.2 g of bis[p-(dimethylamino)phenyl]ethanedione, 2.5 g of 5-chloro-3-formylindole and 5 g of ammonium acetate were refluxed in 17 ml of glacial acetic acid for two hours by heating to effect the reaction. After cooling, the reaction mixture was added dropwise to the mixture of 20 ml of aqueous ammonia and 150 ml of water to precipitate yellowish green crystals. The crystals were collected by filtration, and washed with water. After drying, they were recrystallized with benzene-ethyl acetate ester (1:1) to obtain the compound (7). Melting point; 179°–182° C.

The reaction (color-forming reaction) between the reagent of the present invention and hydrogen peroxide can be illustrated, for example, by the equation (II).

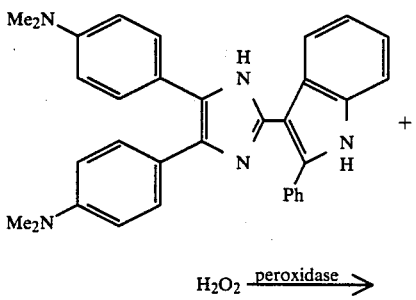

-continued

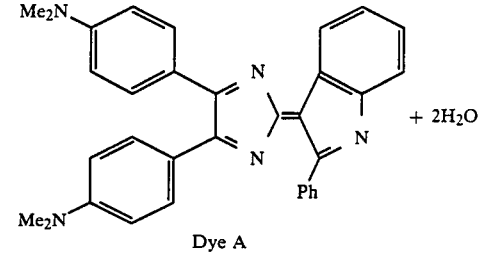

Dye A

The peroxidase used in the present invention serves as a catalyst for an oxidation reaction of hydrogen donor by hydrogen peroxide. Examples of peroxidases suitable for use in the present invention are peroxidase [EC 1.11.1.7] derived from vegetable and animal disclosed in Japanese Patent Publication Nos. 56(1981)-45599 [U.S. Pat. No. 3,983,005], 57(1982)-5520, etc. and peroxidase [EC 1.11.1.7] derived from microorganism disclosed in Japanese Patent Provisional Publication No. 57(1982)-99192, etc. Such peroxidase may be used either alone or as a mixture of two or more of them.

Examples of peroxidases derived from vegetable include those extracted from horse radish, potato, fig sap juice, turnip and radish. Examples of peroxidases derived from animal include lactoperoxidase extracted from milk and verdoperoxidase extracted from leucocyte. Examples of peroxidases derived from microorganism include those derived from microorganism possessing nonspecific peroxidase production ability and belonging to genera Alternaria, Cochliobolus, Curvularia and Pellicularia.

Among them, nonspecific peroxides derived from vegetable or microorganism are preferred.

In addition, instead of peroxidase, there can be used inorganic compounds having peroxidase activity, such as iron thiocyanate, iron tannate, iron ferrocyanide (all compounds being divalent (+2) iron compounds), potassium chromate sulfate, sodium iodide, potassium iodide, ammonium molybdate and potassium molybdate disclosed in Japanese Patent Publication Nos. 56(1981)-45599, 57(1982)-5520, etc.

By using an oxidase in combination with the imidazole derivative of the formula (I) and peroxidase in the present invention, said analytical reagent can be employed more widely. When an analyte or a final intermediate product derived from the analyte can produce hydrogen peroxide under the action of an oxidase, the oxidase is incorporated in the reagent of the present invention so that it becomes possible to quantitatively determine various substances through quantitative determination of the produced hydrogen peroxide. Practically, glucose, uric acid, cholesterol, triglyceride, lactic acid, creatinine, free fatty acid, glutamate-pyruvate transaminase, glutamate-oxaloacetate transaminase, cholinesterase, creatine phosphokinase and lactate dehydrogenase in body fluid (such as blood) and urine, etc. can be determined. Examples of said oxidases which can be used for the measurement include glucose oxidase, uricase, cholesterol oxidase, L-α-glycerophosphate oxidase and pyruvate oxidase. The oxidase may be derived from any origin.

The reagent for analysis of hydrogen peroxide in the present invention is prepared in such a manner that each component is prepared in the form of independent solid material (powder or granule), an aqueous solution or suspension which may be buffered, and when used, that is, when a sample to be analyzed is subjected to quantitative analysis, these components are combined together and used. Alternatively, a mixture of all solid materials (in the form of powder or granule), or an aqueous solution or suspension (which may be buffered) containing all components can be previously prepared and used. When the reagent is used in the form of a solution or suspension containing all components, the aqueous solution or suspension which may be buffered can be prepared by dissolving each component simultaneously or in an appropriate order.

In the case that the reagent for analysis of hydrogen peroxide in the present invention is employed in the form of the aqueous solution or suspension, a solvent of the imidazole derivatives represented by the formula [I] (such as acetone, dimethlyformamide, methanol and ethanol) and a surfactant (a nonionic surfactant such as polyoxyethylene alkylphenyl ether is preferable) are preferably employed.

The reagent for analysis of hydrogen peroxide in the present invention is particularly suitable for use in an integral multilayer chemical-analytical element (film or sheet) wherein a reagent layer and a porous spreading layer (or a porous layer having a definite surface area) in this order are provided on a water-impermeable, light-transmissive support. In a preferred embodiment, each component of the reagent of the present invention is contained in the reagent layer (or said reagent layer and other layer which is provided, if necessary) of said element. Such application is disclosed in Japanese Patent Provisional Publication Nos. 49(1974)-53888 [U.S. Pat. No. 3,992,158], 50(1975)-137192 [U.S. Pat. No. 3,983,005], 51(1976)-40191 [U.S. Pat. No. 4,042,335], 55(1980)-90859, 55(1980)-164356 [U.S. Pat. No. 4,292,272], and 57(1982)-66359, Japanese Utility Model Provisional Publication No. 57(1982)-42951, etc.

As the support, a sheet or a laminate having a thickness in the range from about 10 μm to about 0.5 mm, preferably from about 20 μm to about 0.3 mm and being clear in the range from near-ultraviolet to near infrared regions is employed. Such a sheet or a laminate may be made from a polyester (for example, polyethylene terephthalate or polycarbonate of bisphenol), a cellulose ester (for example, cellulose diacetate, cellulose triacetate, cellulose acetate proprionate, cellulose acetate butyrate and cellulose nitrate), polystyrene or optical glass. A sheet on which a parting agent such as silicone resin is applied is put on the support, and utilized as a protector. Such a sheet may be selected from the above-mentioned supports and other sheets (a semipermeable or opaque sheet such as paper, a plastics and a metal leaf may be employed.). At the time of measurement, this sheet is usually peeled off.

The reagent layer may be comprised a hydrophilic polymer binder such as gelatin, polyvinyl alcohol or polyacrylamide which is disclosed in Japanese Patent Provisional Publication Nos. 49(1974)-53888 [U.S. Pat. No. 3,992,158], 53(1978)-26188, 55(1980)-164356 [U.S. Pat. No. 4,042,335], etc., and an imidazole derivative represented by the formula (I) and, if necessary, other components such as an enzyme which are dispersed homogeneously in the polymer binder. As the other embodiment of the reagent layer, a layer of a hydrophilic polymer binder where hydrophobic particulates containing one or more reagents are dispersed is also included. This layer is disclosed in Japanese Patent Provisional Publication No. 56(1981)-8549.

The porous spreading layer spreads a liquid sample. Various non-fibrous isotropically porous spreading layers, such as membrane filter (blushed polymer layer) disclosed in Japanese Patent Provisional Publication No. 49(1974)-53888 [U.S. Pat. No. 3,992,158], a continuous microspaces-containing porous layer where polymer particulates, glass particulates or diatomaceous earth are dispersed in a hydrophilic polymer binder, a continuous microspaces-containing porous layer where polymer particulates, glass particulates, etc. are joined so as to contact with each other at a point by using a polymer adhesive which does not swell in water (three-dimensional lattice structure layer) disclosed in Japanese Patent Provisional Publication No. 55(1980)-90859 [U.S. Pat. No. 4,258,001], and various fibrous porous spreading layers, such as a textile spreading layer disclosed in Japanese Patent Provisional Publication No. 55(1980)-164356, a knitted spreading layer disclosed in Japanese Patent Application No. 59(1984)-79158 and a spreading layer comprising a paper containing a fibrous pulp of an organic polymer disclosed in Japanese Patent Provisional Publication No. 57(1982)-148250 may be utilized.

Various layers disclosed in the specifications of the above-mentioned patent applications may be introduced into the multylayer element of the invention. Such layers include a registration layer, a light-shielding layer, a light-reflecting layer, a filter layer, a semipermeable membrane layer, a barrier layer, a diffusion-hindering layer (migration-inhibiting layer), a water absorption layer and a layer having two or more of the functions mentioned above.

The multilayer chemical-analytical element of the invention may be manufactured according to the method disclosed in the specifications of the foregoing patent applications.

This multilayer element is preferably put in a slide frame disclosed in Japanese Patent Provisional Publication Nos. 54(1979)-156079 [U.S. Pat. No. 4,169,751] and 57(1982)-63452, Japanese Utility Model Provisional Publication No. 56(1981)-142454 [U.S. Pat. No. 4,387,990], PCT application Japanese National Publication No. 58(1983)-501144 [WO 83/00391], etc. Besides, this multilayer element may be in a form of a long tape, or a clear portion or clamped portion of the multilayer element may be put in a punched card.

The analytical method of the present invention can be carried out in the following manner. An imidazole derivative having the formula (I) and peroxidase (reaction catalyst) in the form as mentioned above are added simultaneously or in appropriate order to a sample to be analyzed. The reaction of the mixture is allowed to proceed at a temperature of from 5° C. to 40° C., preferably 20° C. to 40° C. at a pH of from 3.0 to 9.0, preferably 4.5 to 8.0 for one to 60 minutes, and the absorbance of the reaction mixture containing the formed color is photometrically measured. Alternatively, the imidazole derivative and peroxidase are incorporated in the multilayer chemical-analytical element (film or sheet) described in the aforementioned patent specifications. About 6 to about 15 μl of a sample solution to be analyzed is spotted on the porous spreading layer of said element, or a certain amount of the sample solution in the range of about 10 to about 30 μl is spotted on the porous layer having a definite surface area, and incubated at a temperature of from 20° C. to 40° C., preferably 25° C. to 40° C. for one to twenty minutes, preferably two to ten minutes, and the optical density of the colored area of the multilayer chemical-analytical element is measured through reflection photometry. The measurement of absorbance or reflection optical density can be conducted by any of an end point method and a reaction rate method.

When an oxidase is used in combination, $H_2O_2$ may be previously produced under the action of the oxidase, but it is preferred that the $H_2O_2$-producing reaction and color reaction are allowed to proceed simultaneously. The amount of the oxidase to be used varies depending on the type of the oxidase, the substrate to be analyzed and other contained materials.

As shown in the reaction equation (II), an imidazole compound having the formula (I) reacts with hydrogen peroxide in a stoichiometric amount under the catalytic action of peroxidase to form a dye so that it is possible to analyze or quantitatively determine the peroxidase activity in a sample by adding or spotting the sample having unknown peroxidase activity to or on a reagent comprised of the imidazole compound having the formula (I) and $H_2O_2$ in combination or a multilayer chemical-analytical element containing both. This method can be applied to enzyme-immunoassay using peroxidase as a label substance.

It should be understood that the present invention can be applied to analyze hydrogen peroxide or an analyte capable of producing hydrogen peroxide in body fluid such as blood or urine of not only human being, but also animals such as poultry, pet and laboratory animals.

The reagent of the present invention is characterized in that hydrogen peroxide produced from an analyte can be quantitatively determined with high sensitivity, because the reagent can produce one molar dye from one molar hydrogen peroxide. The analytical reagent, the analytical method and the multilayer chemical-analytical element of the present invention are particularly suitable for use in the determination of hydrogen peroxide in a sample containing a trace amount of hydrogen peroxide (or an analyte capable of forming hydrogen peroxide) as an analyte. The reactivity of the analytical reagent of the invention is well, and the analytical procedure using this reagent is simple. A large number of samples may be treated by using the method of the invention, and this method is suitable for a clinical test.

The following examples are given to illustrate the present invention in more detail.

EXAMPLE 1

(1) Preparation of Color-Forming Solution

A color-forming solution was prepared so as to make the total volume 25 ml by dissolving 15 mg of the compound (4) in acetone and dissolving 5,000 U of peroxidase [EC 1.11.1.7] in an aqueous borate buffer solution (pH 7.5).

(2) Determination of hydrogen peroxide 3 ml of the color-forming solution was placed in a sample cell and 20 μl of hydrogen peroxide having a known content was added thereto. As control, a blank solution was prepared by adding distilled water in place of the aqueous hydrogen peroxide solution. After standing at 37° C. for 10 seconds, the absorbance was photometrically measured at a wavelength of 640 nm. The results are set forth in the following table.

| Content of Hydrogen Peroxide (M/l) | Absorbance |
| --- | --- |
| 0 (blank) | 0.14 |
| $8 \times 10^{-4}$ | 0.41 |
| $1 \times 10^{-3}$ | 0.47 |
| $2 \times 10^{-3}$ | 0.82 |
| $4 \times 10^{-3}$ | 1.52 |

EXAMPLE 2

The surface of a transparent polyethylene terephthalate (PET) film (thickness 185 μm) having a gelatin subbing layer was coated with a coating solution for formation of a reagent layer consisting of the following components, and dried.

Numerical values given below are expressed by the content of each component in each layer after drying.

| Components of Coating Solution for Reagent Layer (solvent: appropriate amount of water) | |
| --- | --- |
| Uricase [EC 1.7.3.3] | 150 U/m² |
| Compound (4) | 0.2 g/m² |
| Peroxidase [EC 1.11.1.7] | 2,500 U/m² |
| Gelatin | 10 g/m² |
| pH 8.5 Borate buffer composition | |

The prepared reagent layer was wetted with water. A cellulose acetate membrane filter (maximum pore size 3.0 μm, thickness 180 μm, Microfilter FM-300 (trademark) manufactured by Fuji Photo Film Co., Ltd., Japan) serving as a porous spreading layer was laminated thereon to obtain an integrated multilayer chemical-analytical element for quantitative determination of uric acid.

For evaluating the resulting multilayer chemical-analytical element, 10 μl of each of aqueous uric acid solutions (content; 6, 10 and 12 mg/dl) and a blank solution containing no uric acid, was spotted on the porous spreading layer and incubated at 37° C. for two minutes. Immediately thereafter, the optical density of the formed color was measured at a measuring wavelength in the vicinity of 630 nm from the PET film side through reflection photometry by means of Macbeth reflection densitometer equipped with a cyan filter. Thus, the following results were obtained.

| Uric Acid Solution (content, mg/dl) | Reflection Optical Density |
| --- | --- |
| 0 (blank) | 0.41 |
| 6 | 1.05 |
| 10 | 1.33 |
| 12 | 1.42 |

It is apparent from the results that the content of uric acid can be determined by reflection photometry and colorimetry using the above multilayer chemical-analytical element.

EXAMPLE 3

The surface of a transparent PET film (thickness 185 μm) having a gelatin subbing layer was coated with a coating solution for formation of a reagent layer consisting of the following components, and dried.

| Components of Coating Solution for Reagent Layer (solvent: appropriate amount of water) | |
| --- | --- |
| Uricase [EC 1.7.3.3] | 200 U/m$^2$ |
| Compound (7) | 0.25 g/m$^2$ |
| Gelatin | 10 g/m$^2$ |
| Peroxidase [EC 1.11.1.7] | 3000 U/m$^2$ |
| Octylphenoxypolyethoxyethanol | 0.15 g/m$^2$ |
| pH 8.5 Borate buffer composition | |

The surface of the resulting reagent layer was coated with a coating dispersion for formation of a light-reflecting layer consisting of the following components, and dried.

| Components of Coating Solution for Light-Reflecting Layer (dispersing medium: appropriate amount of water) | |
| --- | --- |
| Particulate titanium dioxide powder | 3 g/m$^2$ |
| Gelatin | 1 g/m$^2$ |
| Octylphenoxypolyethoxyethanol | 0.1 g/m$^2$ |

Further, the surface of the resulting light-reflecting layer was coated with a coating solution for formation of an interfacing substance-removing layer consisting of the following components, and dried.

| Components of Coating Solution for Interfering Substance-Removing Layer (solvent: appropriate amount of water) | |
| --- | --- |
| Ascorbate oxidase [EC 1.10.3.3] | 4,000 U/m$^2$ |
| Gelatin | 4 g/m$^2$ |
| pH 8.5 Borate buffer composition | |

The resulting interfering substance-removing layer was wetted with water. A No. 100S count cotton broadcloth (a cloth which was washed with water, defatted and dried) was laminated thereon to obtain an integrated multilayer chemical-analytical element for quantitative determination of uric acid.

In a similar manner to that described in Example 2, the reflection optical density of a color formed from uric acid of known content was measured on the multilayer chemical-analytical element.

| Uric Acid Solution (content, mg/dl) | Reflection Optical Density |
| --- | --- |
| 0 (blank) | 0.26 |
| 6 | 0.69 |
| 10 | 0.90 |
| 12 | 0.99 |

EXAMPLE 4

The surface of a transparent PET film (thickness 185 μm) having a gelatin subbing layer was coated with a coating solution for formation of a reagent layer consisting of the following components, and dried to form a second reagent layer.

| Components of Coating Solution for Second Reagent Layer (solvent: appropriate amount of water) | |
| --- | --- |
| Peroxidase [EC 1.11.1.7] | 5,000 U/m$^2$ |
| Compound (7) | 1 g/m$^2$ |
| Gelatin | 10 g/m$^2$ |
| Octylphenoxypolyethoxyethanol | 0.15 g/m$^2$ |
| pH 6.5 Borate buffer composition | |

The surface of the resulting reagent layer was coated with a coating dispersion for formation of a light-reflecting layer consisting of the following components, and dried to form a light-reflecting layer.

| Components of Coating Dispersion for Light-Reflecting Layer (dispersing medium: appropriate amount of water) | |
| --- | --- |
| Particulate titanium dioxide powder | 3 g/m$^2$ |
| Gelatin | 1 g/m$^2$ |
| Octylphenoxypolyethoxyethanol | 0.1 g/m$^2$ |

The surface of the resulting light-reflecting layer was coated with a coating solution for formation of a reagent layer consisting of the following components, and dried to form a first reagent layer.

| Components of Coating Solution for First Reagent Layer (solvent: appropriate amount of water) | |
| --- | --- |
| Cholesterol oxidase [EC 1.1.3.6] | 2,000 U/m$^2$ |
| Gelatin | 10 g/m$^2$ |
| Octylphenoxypolyethoxyethanol | 0.1 g/m$^2$ |
| pH 6.5 Phosphate buffer composition | |

The first reagent layer was wetted with water. A cellulose acetate membrane filter (maximum pore size 3.0 μm, thickness 180 μm, Microfilter FM-300 (trademark) manufactured by Fuji Photo Film Co., Ltd.) was laminated thereon by slightly pressing it to integrate them, whereby providing a porous spreading layer. Thus, a multilayer chemical-analytical element for quantitative determination of cholesterol.

For evaluating the above multilayer chemical-analytical element, 10 μl of each of cholesterol-containing control serums (cholesterol content; 50, 100, 200, 300 and 500 mg/dl) and a blank solution containing no cholesterol was spotted on the spreading layer and incubated at 37° C. for 10 minutes. Immediately thereafter, the optical density of the formed color was photometrically measured at a measuring wavelength of 600 nm from the PET film side through reflection photometry by means of Macbeth reflection densitometer equipped with a cyan filter. The following results were obtained.

| Cholesterol-Containing Control Serum (content, mg/dl) | Reflection Optical Density |
| --- | --- |
| 0 (blank) | 0.26 |
| 50 | 0.49 |
| 100 | 0.68 |
| 200 | 0.98 |
| 300 | 1.18 |
| 500 | 1.48 |

It is apparent from the results that the content of cholesterol can be determined by reflection photometry and colorimetry using the above multilayer chemical-analytical element.

We claim:

1. A reagent for analysis of hydrogen peroxide, which comprises an imidazole derivative having the formula (I):

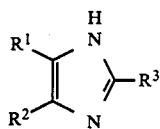

wherein R¹ and R² may be the same or different and are 4-(dimethylamino)phenyl or 4-(diethylamino)phenyl, and R³ is 2-phenyl-3-indolyl or 5-chloro-3-indolyl.

2. The reagent as claimed in claim 1, which further comprises peroxidase.

3. The reagent of claim 1 wherein R¹ and R² are the same.

4. The reagent of claim 1 wherein the imidazole derivative is 2-(2-phenyl-3-indolyl)-4,5-di[4-(dimethylamino)phenyl]imidazole.

5. In a method for the analysis of hydrogen peroxide wherein hydrogen peroxide is reacted with a reagent to form a color and the color is then detected, the improvement which comprises said reagent being
an imidazole derivative having the formula (I):

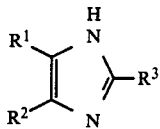

wherein R¹ and R² may be the same or different and are 4-(dimethylamino)phenyl or 4-(diethylamino)phenyl, and R³ is 2-phenyl-3-indolyl or 5-chloro-3-indolyl, to form a color,
and detecting the formed color.

6. The method as claimed in claim 5, wherein the reaction is carried out in the presence of peroxidase.

7. The method as claimed in claim 5 or 6, wherein the detection of the color is conducted by colorimetry, and the method is a quantitative analysis method.

8. The method of claim 5 wherein R¹ and R² are the same.

9. The method of claim 5 wherein the imidazole derivative is 2-(2-phenyl-3-indolyl)-4,5-di[4-(dimethylamino)phenyl]imidazole.

10. A method of analysis of peroxidase which comprises reacting an imidazole derivative having the formula (I) and hydrogen peroxide in the presence of peroxidase:

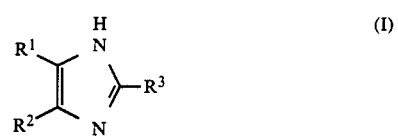

wherein R¹ and R² may be the same or different and are 4-(dimethylamino)phenyl or 4-(diethylamino)phenyl, and R³ is 2-phenyl-3-indolyl or 5-chloro-3-indolyl.

11. The method of claim 10 wherein R¹ and R² are the same.

12. The method of claim 10 wherein the imidazole derivative is 2-(2-phenyl-3-indolyl)-4,5-di[4-(dimethylamino)phenyl]imidazole.

13. A multilayer chemical-analytical element comprising in this order, a water-impermeable, light-transmissive support, a reagent layer and a spreading layer,
which is characterized in that an imidazole derivative having the formula (I) is contained in said reagent layer:

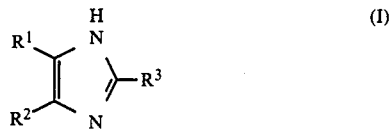

wherein R¹ and R² may be the same or different and are 4-(dimethylamino)phenyl or 4-(diethylamino)phenyl, and R³ is 2-phenyl-3-indolyl or 5-chloro-3-indolyl.

14. The element as claimed in claim 13, which further contains peroxidase.

15. The element as claimed in claim 13 or 14, wherein the porous layer is a porous layer having a definite surface area.

16. The element of claim 13 wherein R¹ and R² are the same.

17. The element of claim 13 wherein the imidazole derivative is 2-(2-phenyl-3-indolyl)-4,5-di[4-(dimethylamino)phenyl]imidazole.

* * * * *